(12) United States Patent
Fischer

(10) Patent No.: US 6,905,335 B2
(45) Date of Patent: Jun. 14, 2005

(54) DENTAL RENEWAL KIT AND METHOD FOR RENEWING A PATIENT'S TEETH

(75) Inventor: Dan E. Fischer, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 148 days.

(21) Appl. No.: 10/289,700

(22) Filed: Nov. 7, 2002

(65) Prior Publication Data

US 2004/0091839 A1 May 13, 2004

(51) Int. Cl.[7] ............................................... A61C 13/38
(52) U.S. Cl. ...................................... 433/77; 433/215
(58) Field of Search ................................ 433/226, 215, 433/77; 206/63.5, 369, 368

(56) References Cited

U.S. PATENT DOCUMENTS

| | | | | |
|---|---|---|---|---|
| 1,684,417 A | * | 9/1928 | Silberman | 206/229 |
| 4,293,074 A | * | 10/1981 | Dunsky | 206/572 |
| 5,217,372 A | | 6/1993 | Truocchio | 433/215 |
| 5,289,919 A | | 3/1994 | Fischer | 206/571 |
| 5,425,641 A | | 6/1995 | Fischer | 433/226 |
| 5,660,546 A | | 8/1997 | Shafer | 433/216 |
| 6,022,218 A | | 2/2000 | Alpert | 433/215 |
| 6,079,979 A | | 6/2000 | Riitano | 433/81 |
| 6,135,771 A | | 10/2000 | Dragan et al. | 433/90 |
| 6,187,294 B1 | * | 2/2001 | Penner | 424/49 |
| 6,213,771 B1 | * | 4/2001 | Fischer | 433/75 |
| 6,217,335 B1 | * | 4/2001 | Riitano et al. | 433/224 |
| 6,312,258 B1 | | 11/2001 | Ashman | 433/172 |
| 2003/0026770 A1 | * | 2/2003 | Szymaitis | 424/50 |

* cited by examiner

*Primary Examiner*—Melba Bumgarner
(74) *Attorney, Agent, or Firm*—Workman Nydegger

(57) ABSTRACT

A kit includes a group of predetermined components for enabling a dental hygienist or technician to perform non-invasive dental renewal procedures. The kit includes one or more abrasive devices, one or more restorative compositions, and one or more delivery tips for applying the restorative compositions. The abrasive device comprises one or more of a low-speed dental bur, a prophylaxis cup, brush, paste or jet. The kit may also include a delivery device, e.g., a syringe, or a storage device for storing the restorative composition.

38 Claims, 6 Drawing Sheets

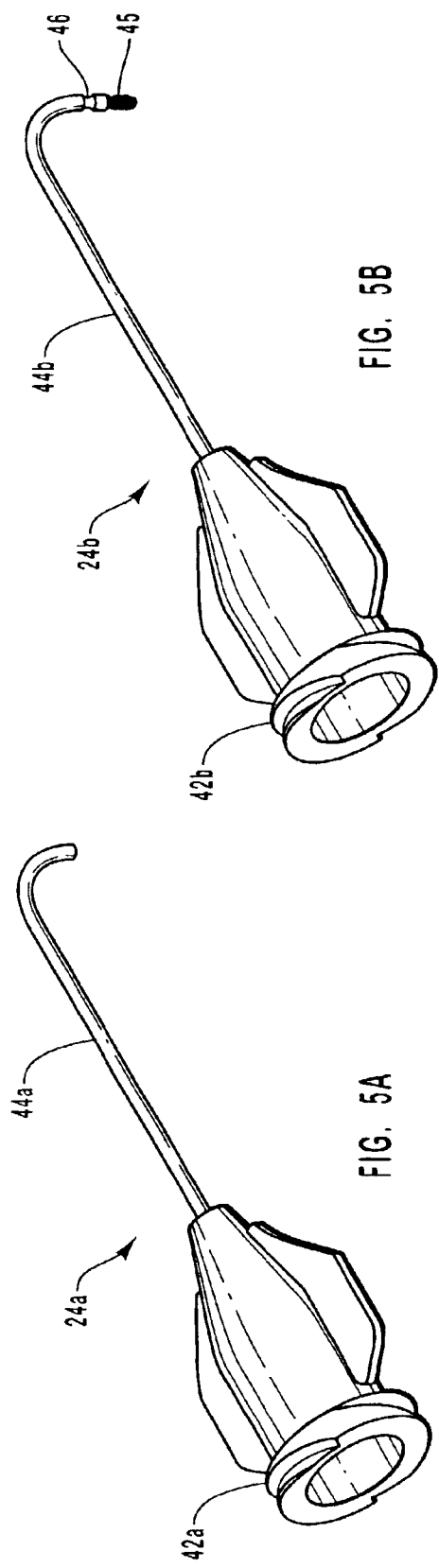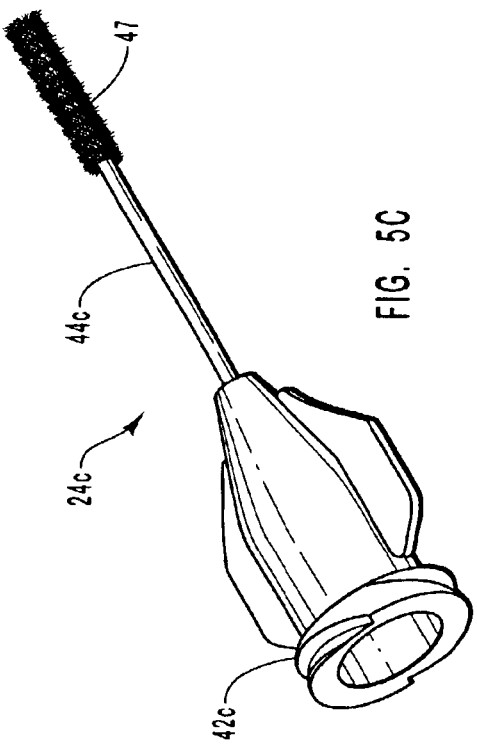
FIG. 5A
FIG. 5B
FIG. 5C

DENTAL RENEWAL KIT AND METHOD FOR RENEWING A PATIENT'S TEETH

BACKGROUND OF THE INVENTION

1. The Field of the Invention

The present invention relates to dental renewal procedures. More particularly, the present invention relates to kits that facilitate non-invasive dental renewal procedures by a dental hygienist or other dental technician.

2. The Relevant Technology

For over the last 15 years, the demand for dental renewal has increased due to advances in dental technology. Dental renewal includes repairing previous dental work by applying a restorative composition. This is also known as dental restoration or dental repair. For example, dental renewal includes repairing previous dental work such as repairing the bond interface between dental fillings and tooth enamel, repairing crowns or bridges, and other minor defects that do not require invasive dental procedures. Because of increased demand for dental renewal, a dentist could potentially become distracted or preoccupied by such procedures, thereby impinging on the time required for more traditional or invasive procedures, where the dentist's skills are more needed.

Dental renewal may range from extremely noninvasive to extremely invasive procedures, depending on the particular case. It is often the case that many dental renewal procedures are relatively non-invasive (e.g., Class I) and can be done relatively quickly. However, a dentist has heretofore been responsible for performing virtually all dental renewals, both invasive and noninvasive. In general, the dentist's expertise allows the dentist to know which equipment and which restorative compositions should be used for a given procedures. Second, the equipment in the dentist's office is usually widely applicable for a variety of dental procedures, and, thus, unsafe or even illegal for a dental hygienist or dental technician to operate instead of the dentist, or at least without close supervision. Where close supervision is provided by a dentist, it will be appreciated that this distracts the dentist from being able to perform other dental procedures.

Thus, it would be an improvement in the art of dentistry to provide specialized kits that facilitate specific noninvasive dental renewal procures to be safely and effectively performed by a dental hygienist or other dental technician without the immediate supervision of a dentist.

BRIEF SUMMARY OF THE INVENTION

The present invention relates generally to dental renewal or touch up kits for use by non-dentist practitioners (e.g., dental hygienists or dental technicians) to repair minor defects in crowns, fillings, and/or other dental work. Specifically, the present invention is directed to a set of components which are pre-grouped as a kit to allow a dental hygienist or dental technician to safely perform a dental renewal without damaging the patient's teeth. The present invention also relates to methods of using a set of predetermined components which allow a dental hygienist or dental technician to perform various non-invasive dental renewal procedures.

A first component of the kit is an abrasion device for abrading an area of a tooth or dental work. In one embodiment, the abrasion device is a dental bur that is only capable of being operated at low speed. The dental bur may be included by itself or with a low-speed dental hand piece to operate the dental bur. The use of high-speed dental hand pieces are generally excluded from the present invention. If it is desired to include a high-speed dental bur within the kits of the present invention, the kits will also typically include a high-speed to low-speed adaptor to ensure that the dental bur is not inadvertently operated in a high-speed dental hand piece.

In general, low-speed dental burs are configured with a shaft which only fits a low-speed dental hand piece so that the low-speed dental bur cannot be used with a high-speed dental hand piece. If a high-speed dental bur is included in the kit, an adaptor may be included which modifies the shaft of the high-speed dental bur so that it will fit a low-speed dental hand piece. The dental bur is intended to operate with a low-speed hand piece in order to provide a dental hygienist or dental technician with a tool suitable for relatively non-invasive procedures.

In another embodiment, the abrasion device can be a prophylaxis cup or brush which may be used with an abrasive paste. The prophylaxis cup or brush is also configured to operate with a low-speed dental hand piece. Thus, a trained dental hygienist or dental technician may be able to abrade a particular area of a tooth or dental work as part of a renewal procedure in embodiments that utilize prophylaxis paste.

A second component of the kit is a restorative composition. Generally, the restorative composition may be any composition used in dental renewal. Examples include, but are not limited to, acid etches, primers, bonding agents, sealants, cements, and composites. The restorative compositions may be provided in bulk containers such as jars or tubes; or they may be pre-loaded within a delivery device such as a syringe.

The third component of the kit is a delivery tip for use with syringe delivery devices in or to place the restorative composition(s) at the intended site of the tooth. The syringe delivery device may or may not be preloaded with the restorative composition. In a preferred embodiment, the delivery tips have 28–32 gauge cannulas, with 30–31 gauge cannulas being most preferred.

The above-described components may advantageously be assembled in a kit to provide a dental hygienist or dental technician with the components necessary to perform non-invasive dental renewal procedures. Such kits are suitable for performing Class I sealing and filling restorations and repair procedures.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 5A illustrates one embodiment of a delivery tip for use in the present invention;

FIG. 5B illustrates another embodiment of a delivery tip for use in the present invention;

FIG. 5C illustrates yet another embodiment of a delivery tip for use in the present invention;

DETAILED DESCRIPTION OF THE PREFERRED EMBODIMENTS

The present invention encompasses kits for use by non-dentists that provide for relatively non-invasive dental renewal procedures. As used herein, the term "dental renewal procedure" includes repairing previous dental work by applying a restorative composition. The term "dental renewal procedure" is used interchangeably with the terms "dental restoration" or "dental repair."

In general, dental renewal procedures may range from noninvasive to extremely invasive. However, the kits of the present invention are specifically configured for use in carrying out relatively noninvasive procedures which generally fall within the category of dental procedures known as "Class I". The inventive kits facilitate procedures that are sufficiently noninvasive so as to be considered as "touch ups" of previous dental work performed by a licensed dentist (e.g., constructing crowns and/or bridges, filling Class I–V cavities, endodontic procedures and the like). The procedures using kits of the present invention would thus consist of minor repair of previous dental work or other similar noninvasive renewal procedures. The procedures may also include Class I sealing procedures. Thus, as used herein, the term "Class I restoration" includes noninvasive dental renewal procedures which would fall within the Class I category of dental procedures and Class I sealings.

The dental renewal procedures using the kits of the present invention should be performed under the general supervision of a licensed dentist. However, under this general supervision, a dental hygienist or dental technician will be able to perform the dental renewal without the immediate supervision of a dentist. Indeed, in some cases, the dentist need not be present in the room at all while the dental hygienist or dental technician is performing the dental renewal procedures of the present invention, freeing the dentist to perform more complicated and/or invasive procedures.

Figure 1:
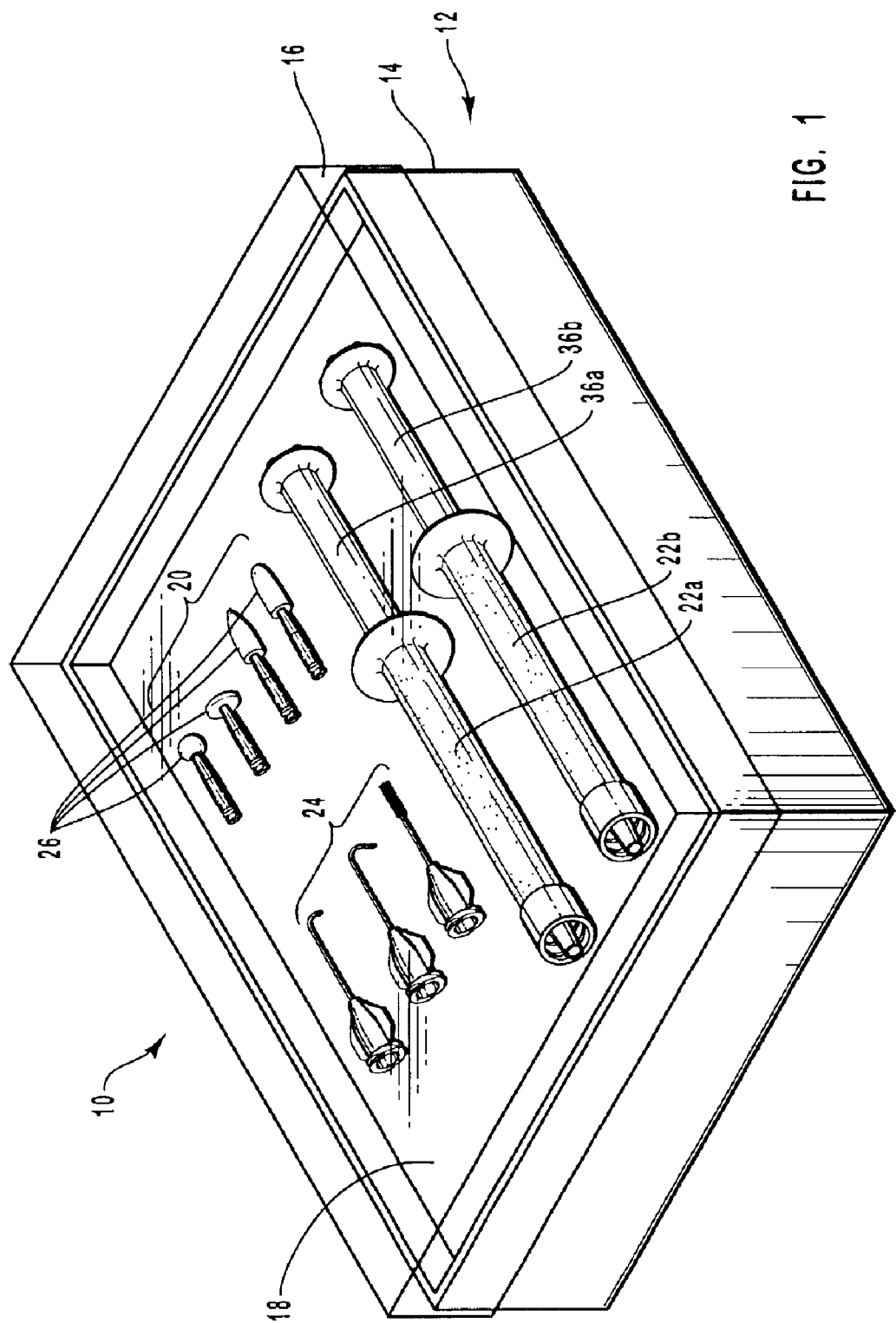
FIG. 1 illustrates an embodiment of a kit of the present invention illustrating exemplary components of the invention.

FIG. 1 shows one embodiment of a kit 10 in accordance with the present invention. Kit 10 comprises a predetermined or pre-grouped set of components that enable a dental hygienist or dental technician to perform a dental renewal procedure. Generally, the components of kit 10 comprise an abrasion device 20, one or more restorative compositions 22, and one or more delivery tips 24. It will thus be appreciated that by using kit 10, a dental hygienist or dental technician is provided substantially all of the tools necessary to perform a relatively non-invasive dental renewal procedure. It will be appreciated that because of the variety of types of dental renewal procedures and the particular needs of the patient, the kits of the present invention may embody numerous different combinations or variations of components each being appropriate for a particular procedure.

As reflected in FIG. 1, the components of kit 10 may be assembled in a container 12 for easy transportation and/or storage of the components grouped therein. Various embodiments for container 12 are contemplated within the scope of this invention, each embodiment generally comprising a base 14, a cover 16, and a structural support 18 for ensuring that the components of 12 are placed in an organized, secure fashion. For example, structural support 18 may comprise a foam insert shaped to receive the various components of kit 10 so that the components are organized, easily retrievable and easily replaceable back into container 12. It will be appreciated that the organization and structural features of kit 10 are purely illustrative and not limiting. The abrasion devices, restorative compositions, and deliver tips may be organized in any desired fashion (or not organized at all).

The first dental renewal component of kit 10 comprises an abrasion device 20. Abrasion device 20 constitutes means for noninvasively abrading a patient's tooth, a dental prosthesis, filling material, or other dental work. As used herein, the term "abrade" means to roughen and/or smooth by gentle grinding. Abrasion results in gently shaping, mildly roughening, smoothing, and/or slightly exposing a particular area of the tooth or dental work. Abrading the site of the tooth or dental work beneficially removes additional plaque and/or contaminants which may remain on the surface after cleaning. This creates a better bonding surface. Further, abrasion can be used to shape the tooth or dental work if needed. For example, a crown may become misaligned with the existing tooth, requiring reshaping an edge or surface of the crown or underlying tooth. Abrading of the tooth or dental work surface also assists in providing a receptive surface or shallow hollow to receive a restorative composition. In general, the means for noninvasively abrading a patient's tooth, a dental prosthesis, filling material, or other dental work comprises noninvasive devices which are suitable for use by a dental hygienist or dental technician.

As shown in FIG. 1, in one embodiment, one specific means for noninvasively abrading a patient's tooth, a dental prosthesis, filling material, or other dental work is a low-speed dental bur 26. Generally, low-speed dental burs 26 are sized and configured to selectively couple to a low-speed dental hand piece 28 (see FIG. 2). As used herein, the term "low-speed" describes a hand piece that operates at a speed of 0–50,000 RPM. These speeds are slow enough to prevent the dental hygienist or dental technician from inadvertently damaging the previous dental work or otherwise going beyond the intended procedure. In addition, these speeds are slow enough to prevent invasive damage to the tooth or dental prosthesis or filling material. As such, a dental hygienist or dental technician can safely use the low-speed dental bur 26 to gently abrade the tooth or dental work. The use of high-speed dental hand pieces (i.e., that operate at 300,000–500,000 RPM) by non-dentists is not recommended.

Figure 2:
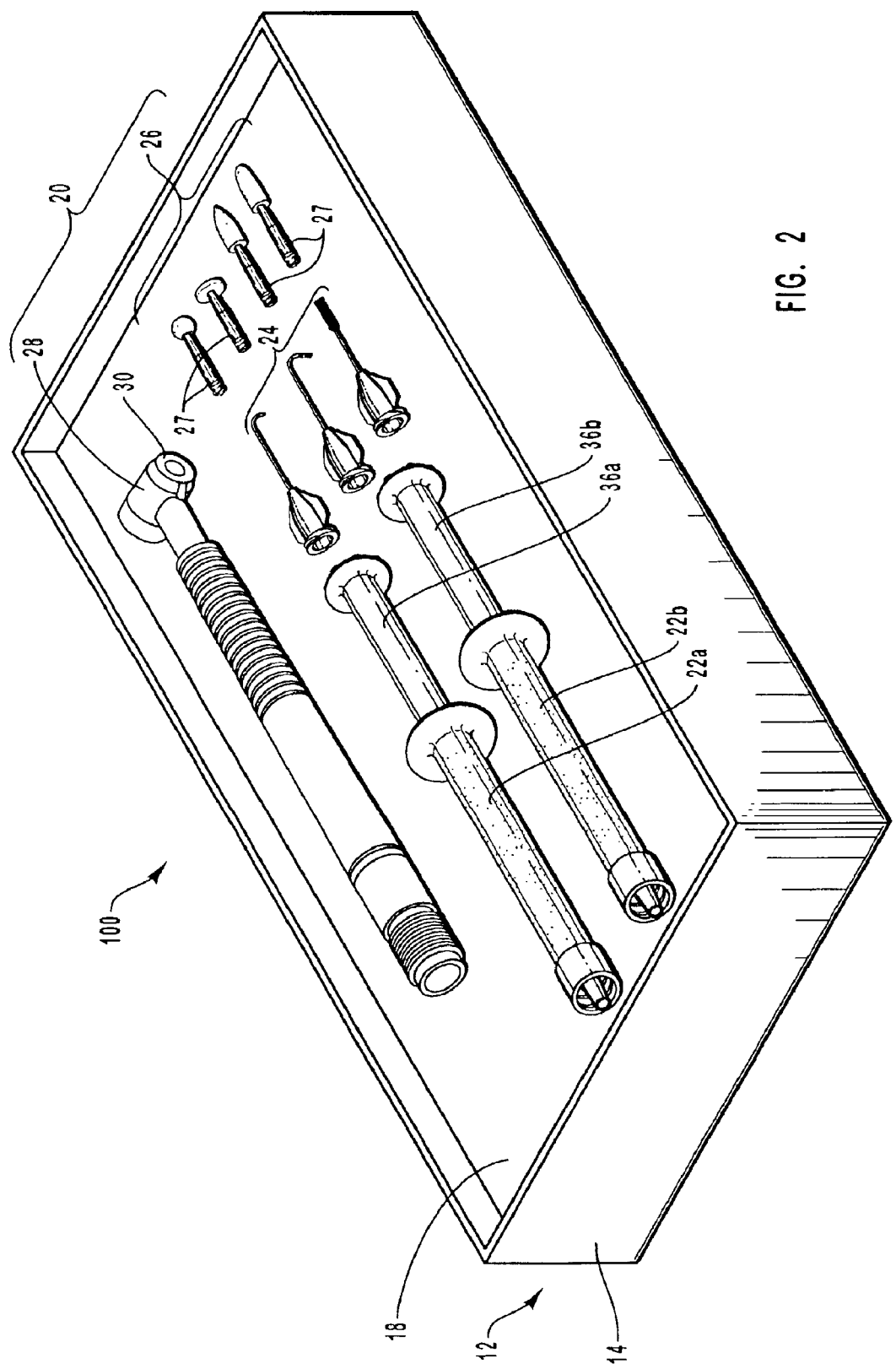
FIG. 2 illustrates another embodiment of a kit of the present invention illustrating a low-speed dental hand piece being provided in the kit and the restorative composition being preloaded in syringe delivery devices.

As seen in FIG. 2, hand piece 28 has a receiving portion 30 configured to receive a corresponding shaft 27 of a dental bur 26. Low-speed dental hand pieces 28 generally have receiving portions 30 configured to receive a dental bur 26 having a larger diameter shaft 27 than a high-speed bur or drill. The shaft of a low-speed dental bur is typically notched to engage a corresponding locking feature of the low-speed hand piece. Thus, low-speed dental burs 26 have a shaft 27 that corresponds to the size of the receiving portion 30 of the low-speed hand piece 28. In contrast, high-speed dental hand piece (not shown) has a smaller receiving portion configured to receive a dental bur (not shown) having a smaller diameter shaft. This prevents a low-speed dental bur 26 from being inadvertently attached to a high-speed dental hand piece because its larger diameter shaft 27 will not fit within the receiving portion of the high-speed hand piece. Other means for preventing the use of a high-speed hand piece would certainly be within the scope of the invention.

In the embodiment of FIG. 1, one or more low-speed dental burs 26 are provided in kit 10 without a dental hand piece. That is, dental burs 26 are intended to be connected to a dental hand piece already existing in the dental office. It is usually the case that the dentist office already has a dental hand piece configured to operate at low-speed. As such, it will be appreciated that the components of this embodiment may be easily transported, shipped, and/or sold to dental offices. As discussed above, because dental hand pieces have standardized sizes, this embodiment may be particularly preferred, especially in order to reduce the shipping cost of the kits of the present invention.

As illustrated in FIG. 2, it is contemplated that a low-speed dental hand piece 28 may be provided in the kits if desired. As depicted in FIG. 2, a kit 100 comprises a low-speed hand piece 28 and one or more low-speed dental burs 26. This embodiment ensures that dental burs 26 are operated at low speeds. Thus, a plurality of dental burs 26 may be provided, each dental bur 26 being selectively couplable to dental hand piece 28. In another embodiment (not shown), a dental bur 26 may be permanently attached to low-speed hand piece 28, further ensuring that dental bur 26 will operate at low speeds.

In another embodiment (not shown), one or more high-speed dental burs may be included in a kit of the present invention together with a standard adapter (not shown) that modifies the diameter of the shaft of the high-speed dental bur so that it can be connected to a low-speed dental hand piece.

Figure 3D:
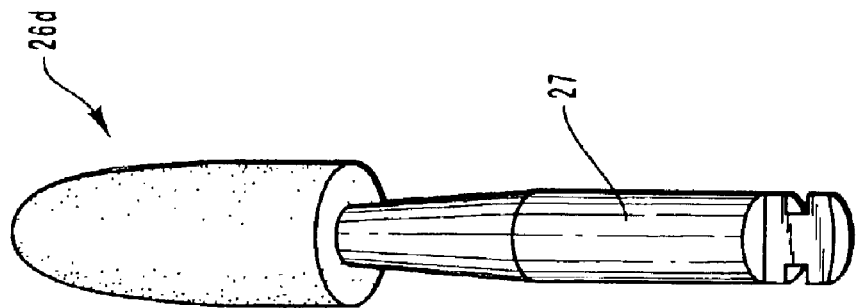
FIG. 3D illustrates a cylindrical dental bur.
Figure 3C:
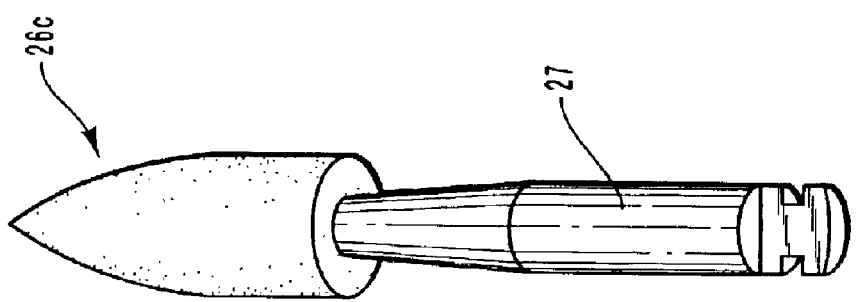
FIG. 3C illustrates a flame tip dental bur.
Figure 3B:
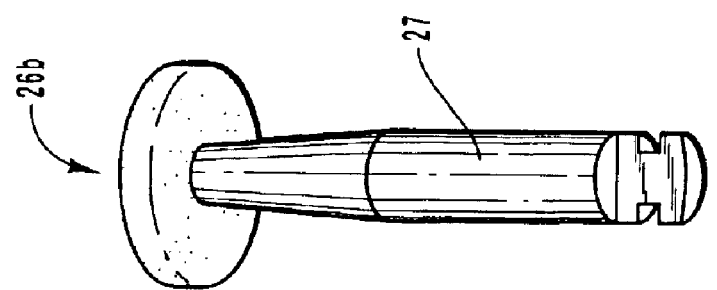
FIG. 3B illustrates a wheel tip dental bur.
Figure 3A:
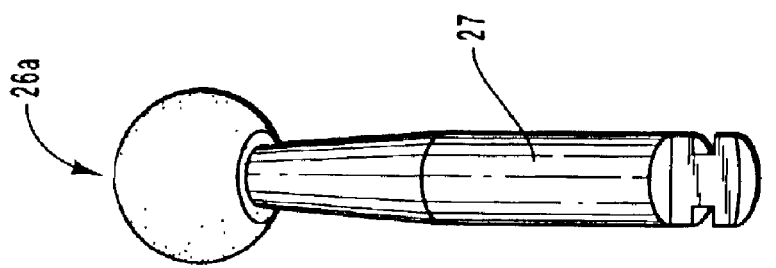
FIG. 3A illustrates a round tip dental bur.

It will be appreciated that a variety of dental burs 26 may be included in the kits of the present invention if desired (as illustrated in FIGS. 1 and 2). FIG. 3A more particularly illustrates a dental bur 26a having a round tip. FIG. 3B illustrates a dental bur 26b with a wheel tip. FIG. 3C depicts dental bur 26c having a flame tip. FIG. 3D illustrates dental bur 26d having a cylindrical tip. Dental burs 26 may be coated with a grit to assist the tip in abrading the surface of the tooth at the particular site. Preferably, a medium grit to ultra fine grit is formed on the outer surface of dental burs 26. It is appreciated that other configurations of dental burs 26 may be included in the kits of the present invention. In each of FIGS. 3–3D, dental burs 26a–26d each have a shaft 27 sized to be received in receiving portion of low-speed dental hand piece 28 (FIG. 2). It is appreciated that low-speed bur 26 and low-speed dental hand piece 28 is but one example of a means for abrading the tooth or dental work at a particular site.

Figure 4:
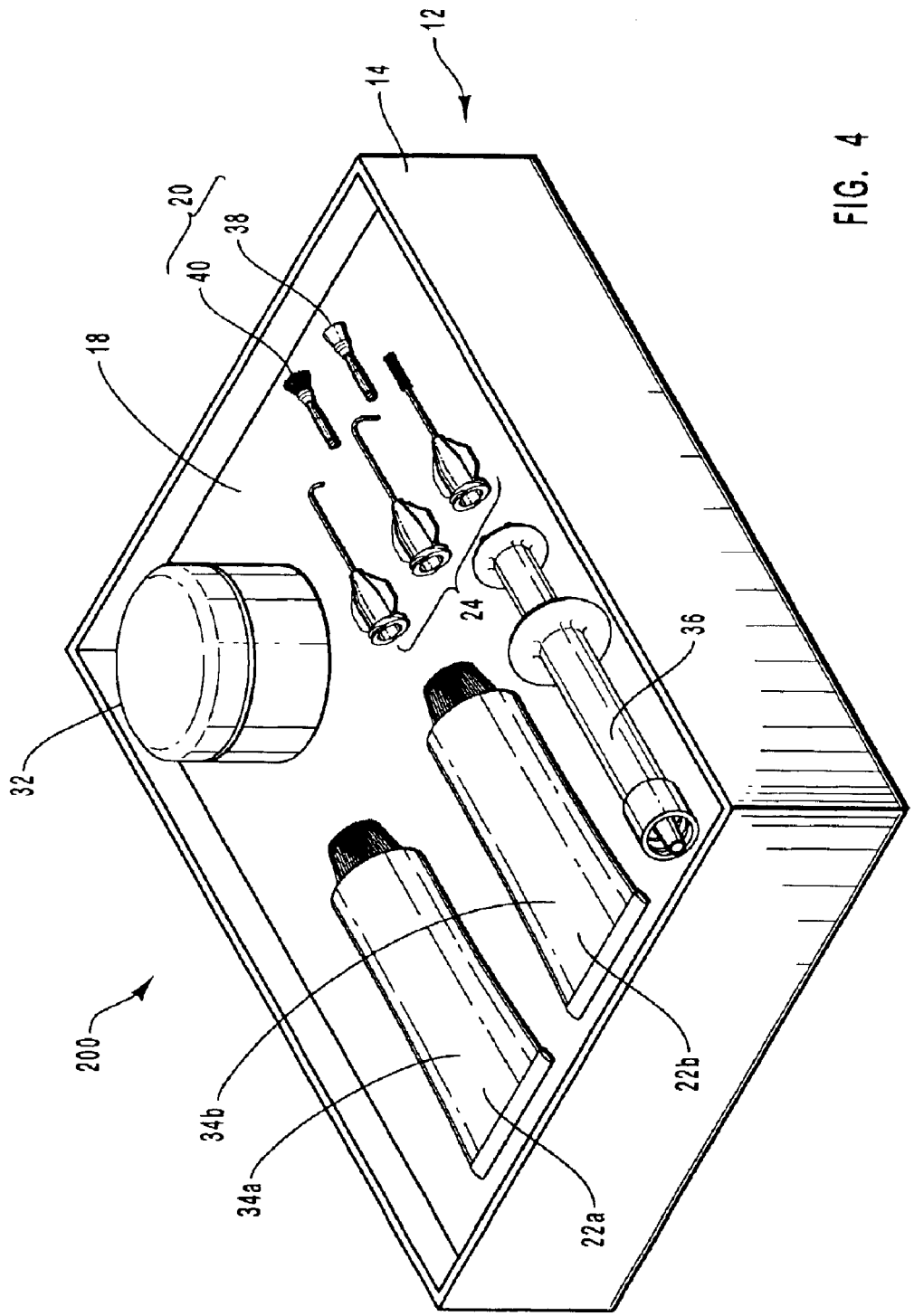
FIG. 4 illustrates another embodiment of a kit of the present invention illustrating a prophylaxis cup and prophylaxis brush being provided in the kit.

As depicted in FIG. 4, a kit 200 is shown to include alternative abrading means 20 in the form of a prophylaxis cup 38 and a prophylaxis brush 40. Prophylaxis cup 38 and prophylaxis brush 40 comprise means for noninvasively abrading a patient's tooth, a dental prosthesis, filling material, or other dental work. Prophylaxis cup 38 and prophylaxis brush 40 are configured to be used in conjunction with an abrasive prophylaxis paste to gently abrade a tooth or dental work. As such, kit 200 is shown to include an abrasive prophylaxis paste 32. Prophylaxis paste 32 may contain an abrasive powder or other component which provides a desired level of abrasion when applying the prophylaxis paste. Prophylaxis cup 38, prophylaxis brush 40 and prophylaxis paste 32 are ideal for dental hygienists or dental technicians that are already well-trained in the use of prophylaxis pastes, prophylaxis brushes, and/or prophylaxis cups.

Like the low-speed dental burs 26 discussed above, prophylaxis cup 38 and prophylaxis brush 40 are sized and configured for attachment to a low-speed dental hand piece. Because prophylaxis cup 38 and prophylaxis brush 40 are operated at low-speed, excessive grinding of the tooth or dental work is avoided. In one embodiment (not shown), a kits according to the invention may include a prophylaxis paste but not a prophylaxis brush or prophylaxis cup in view of the fact that such components may already be available in a dentist's office. In yet another embodiment (not shown), a low-speed dental hand piece may be included in a kit with a prophylaxis paste 32, prophylaxis cup 38, and/or prophylaxis brush 40. Furthermore, prophylaxis paste 32, prophylaxis cup 38, and/or prophylaxis brush 40 may be included in addition to one or more dental burs 26. It is within the scope of the invention to use devices suitable for microabrasia or a prophylaxis jet.

Kits 10, 100 and 200 also include a restorative composition 22. Each restorative composition 22 may be one of a number of existing restorative compositions or may be specifically formulated. Restorative compositions 22 may be used for a variety of purposes during dental renewal procedures. As such, one or more restorative compositions 22 may be provided in the kits of the present invention.

For example, a restorative composition may be used to prepare a specific area of the tooth to receive a filling or sealing restorative composition. Preparatory restorative compositions include, but are not limited to, cleaning agents, acid etches, primers, bonding agents, or drying agents. A cleaning agent may be used to further clean the surface of a particular site after it has been gently abraded. An example of a cleaning agent is CONSEPSIS SCRUB, which is available from Ultradent Products, Inc., located in South Jordan, Utah. A drying agent may be used to dry and prime the surface of a particular site after it has been cleaned or may assist in drying another restorative composition that has already been applied to the particular site. An example of a drying agent is PRIMADRY, sold by Ultradent Products, Inc. An etching agent is used to further roughen the surface of a particular site after it has been roughened by gentle abrasion. ULTRAETCH (sold by Ultradent Products, Inc.) is an example of an etching agent. A priming agent acts as a primer between a particular site and another restorative composition, an example of a priming agent being PERMAQUICK (also available from Ultradent Products, Inc.). A bonding agent assists in bonding a particular site to another restorative composition. Examples of suitable bonding agents are PQ1, PERMASEAL, PERMAQUICK bonding resin, or PQ AMALGAM, which are available from Ultradent Products, Inc.

A filling or sealing restorative composition such as a composite resin may be applied to repair the previous dental work. These types of restorative compositions include a composite resin such as, but not limited to flowable restorative agents, composites, amalgams or porcelains. A flowable restoring agent may function as a sealant. Examples of flowable restorative composites are ULTRASEAL XT and PERMAFLO. An example of a paste composite is AMELOGEN. Examples of unfilled sealants include PERMASEAL and UNIVERSAL DENTAL SEALANT. Each of the foregoing are available from Ultradent Products, Inc.

In summary, restorative compositions 22 may include any composition which may be used during a dental renewal procedure of the present invention. As each dental renewal procedure may require different restorative compositions, it will be appreciated that a specific combination of restorative compositions may be provided in the kits of the present invention for a given procedure.

In the embodiments of FIGS. 1 and 2, restorative compositions 22a, 22b are provided preloaded in one or more syringe delivery devices 36a, 36b. Preferably, syringe delivery devices 36a, 36b will have a cap (not shown) disposed thereon to prevent leaking of the restorative composition. It is appreciated that syringe delivery devices 36a, 36b are only one example of a suitable delivery device for storing and/or delivering a restorative composition to a tooth or dental work. It will be appreciated that restorative compositions 22a, 22b may be the same or different compositions.

In the embodiment of FIG. 4, restorative compositions 22a, 22b may be provided in the kits of the present invention in storage containers 34a, 34b such as a squeezable tube, a bottle, and the like. In these embodiments where a storage container 34 is provided in the kit, when the dental hygienist or dental technician is ready to use the restorative composition 22, he/she simply loads or fills the restorative composition 22 into syringe delivery device 36 for application to a particular site on a tooth. The syringe delivery device 36 may be provided in the kit or provided separately from the kit.

Kits 10, 100, and 200 also include one or more delivery tips 24 for delivering the restorative composition 22 to a particular site on a tooth or dental work. Delivery tips 24 are configured to engage a syringe delivery device 36. As such, delivery tips 24 may have a standard luer lock fitting so as to selectively couple to syringe delivery device 36. Alternatively, delivery tip 24 may be permanently coupled to syringe delivery devices 36.

As shown in more detail in FIGS. 5A–5C, various types of delivery tips 24 may be used within the kits of the present invention. As shown in FIG. 5A, delivery tip 24a comprises a hub 42a which is attached to a cannula 44a and configured so as to be threadably coupled to syringe delivery device 36. Hub 42a may be configured to have a luer-lock connection to selectively couple to a corresponding luer-lock connection on syringe delivery device 36 as is well known in the art. Cannula 44a is a standard curved needle-tip cannula, preferably constructed of metal.

FIG. 5B illustrates a delivery tip 24b having a cannula 44b with a curved-tip having a bundle of fibers 45 disposed at an end thereof. The fibers are held in place by a crimp 46 within the cannula 44b.

FIG. 5C depicts a delivery tip 24c with a cannula 44c having a flocked tip 47.

It will be appreciated that delivery tips 24a–24c are exemplary of the types of delivery tips 24 that may be appropriate in dental renewal procedures of the present invention. However, other delivery tips not herein disclosed are also contemplated and encompassed within the present invention. Preferably, cannula 44 of delivery tip 24 is configured to be able to reach or inserted into small spaces. In one embodiment, cannula 44 is preferably 28–32 gauge. In a more preferred embodiment, cannula 44 is 30-31 gauge. Suitable materials for constructing cannula 44 of delivery tip 24 include plastic and metal.

From the foregoing description, it will be appreciated that all of the components necessary to perform dental renewal is provided in a convenient kit so that a dental hygienist or dental technician may easily and safely perform a dental renewal procedure. The following provides examples of components which may be provided in a set of the present invention.

EXAMPLE 1

The embodiment of FIG. 1 comprises:
1. A plurality of low-speed dental burs
2. A plurality of syringe delivery devices storing different restorative compositions
3. A plurality of delivery tips selectively couplable to the syringe delivery devices

EXAMPLE 2

The embodiment of FIG. 2 comprises:
1. A low-speed dental hand piece
2. A plurality of dental burs selectively couplable to the dental hand piece
3. A plurality of syringe delivery devices storing one or more different restorative compositions
4. A plurality of delivery tips selectively couplable to the syringe delivery devices

EXAMPLE 3

The embodiment of FIG. 4 comprises:
1. An abrasive prophylaxis paste provided in a container
2. A prophylaxis brush
3. A prophylaxis cup
4. A plurality of plastic tubes storing one or more different restorative compositions
5. One or more delivery tips

EXAMPLE 4

Another embodiment of the present invention could comprise:
1. An abrasive prophylaxis paste
2. One or more syringes storing restorative compositions
3. One or more delivery tips Notwithstanding the foregoing, it should be appreciated that the kits according to the present invention may include any combination of abrasion means, restorative compositions and delivery tips as desired to carry out any desired dental renewal procedure.

The method of using the components of the kits of the present invention will now be described. Generally, the dental renewal procedures of the present invention comprise two phases (1) preparing the tooth; and (2) applying a restorative composition to the tooth. It will be appreciated that dental renewal procedures of the present invention are minimally invasive procedures such that they would be safe for dental hygienists and dental technicians to perform.

A site that needs renewing is first identified. The renewal site usually comprises an area where preexisting dental work is located. For example, the renewal site may be the location of an existing dental prosthesis (e.g., a crown) that needs repair. The renewal site may be the location of poor or degraded bond interface between the tooth and dental filling material. The site needing dental renewal may be part of an existing tooth where previous dental work has not been done but which is in need of a simple Class I restoration.

Figure 8:
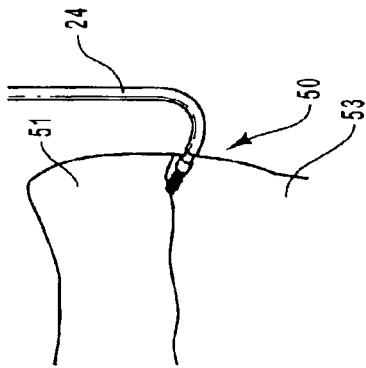
FIG. 8 illustrates application of a restorative composition at the site of FIG. 6, the restorative composition being applied by a delivery tip provided in a kit of the present invention.
Figure 7:
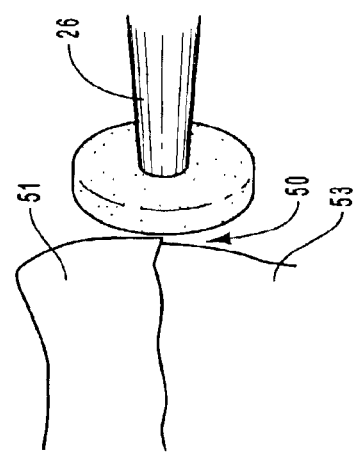
FIG. 7 illustrates application of a low-speed dental bur at the site of FIG. 6.
Figure 6:
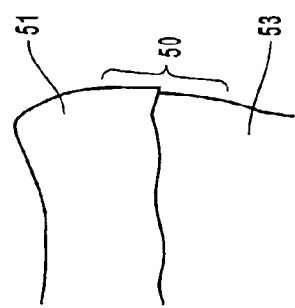
FIG. 6 illustrates an exemplary site of a tooth requiring dental renewal.

FIG. 6 is illustrative of a site 50 of a tooth in need of dental renewal. Site 50 is an example of a crown 51 which needs repair. The edge of crown 51 has become misaligned with the tooth 53. As shown in FIG. 7, preparation of the renewal site includes abrasion of the edge of the crown with a low-speed dental bur 26. As discussed above, gentle abrasion of site 50 may be performed by any means for abrading site 50 including, but not limited to, a low-speed dental bur 26 or an abrasive prophylaxis paste 32. Site 50 can be non-invasively shaped until the crown 51 is substantially flush with the existing tooth 53, as depicted in FIG. 8.

The second phase involves applying a restorative composition. As discussed above, one or more restorative compositions 22 may be provided in the kit. Further, one or more delivery tips 24 may be provided corresponding to the number of restorative compositions. The delivery tip(s) may be selectively coupled to a syringe delivery device 36 which may or may not be included in the kit. In the second phase, the dental hygienist or dental technician simply selects the appropriate restorative composition to apply and attaches an appropriate delivery tip to the syringe delivery device. In the case where the restorative composition is provided in a separate storage container (e.g., a plastic tube or jar), the dental hygienist or dental technician simply loads or fills a syringe delivery device with the restorative composition.

Figure 10:
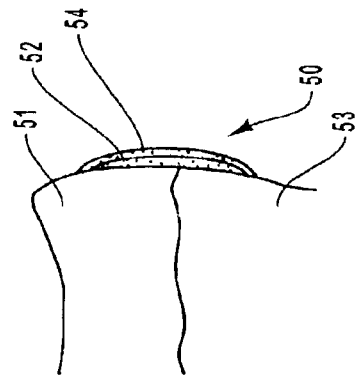
FIG. 10 illustrates a second layer of restorative composition on the site of FIG. 6.
Figure 9:
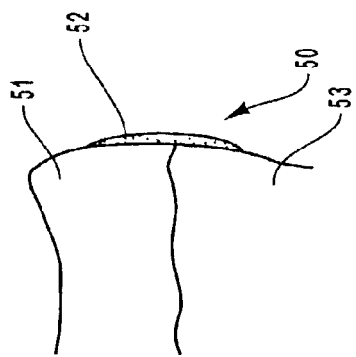
FIG. 9 illustrates a first layer of restorative composition on the site of FIG. 6.

As depicted in FIG. 9, a first layer 52 of restorative composition is applied. The first layer 52 may comprise, for example, an etchant, or bonding agent, or a primer. Some etchants may need to be rinsed off prior to applying subsequent restorative compositions. It will be appreciated that more than one layer of the same or different restorative compositions may be applied to site 50. As shown in FIG. 10, a second layer 54 of a restorative composition different from the first layer may be applied over the first layer 52. The second layer 54 may comprise, for example, a flowable restorative agent or sealant.

As discussed above, one of the delivery tips may comprise a brush to assist in spreading the restorative composition over site 50. After the restorative composition has sufficiently dried, the dental hygienist or dental technician may further abrade the area over site 50 to remove any unevenness or irregularities on the surface of the restorative composition. It will be appreciated that any number of different restorative compositions may be applied as needed to carry out a desired renewal procedure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A kit comprising a pre-packaged set of components specially selected and adapted for use by a dental hygienist or dental technician in performing a noninvasive dental renewal procedure, but not highly invasive dental procedures, the pre-packaged set of components being initially disposed within a kit container prior to use, the components within the kit container comprising:

one or more abrasion devices, each comprising:
an abrading portion; and
a shaft extending from the abrading portion that is adapted to mate with the receiving portion at a low-speed dental hand piece that operates at a speed in a range of 0–50,000 RPM but not with the receiving portion of a high speed dental hand piece that operates at a speed in a range of 300,000–500,000 RPM, the abrading portion being configured so as to be suitable for noninvasively abrading at least one of a patient's tooth, or a dental prosthesis, filling material, or other dental work located within a patient's mouth, during a dental renewal procedure;

one or more dental restorative compositions suitable for application to a tooth in a Class I and/or non-invasive dental renewal procedure; and one or more delivery tips adapted for delivery of the one or more restorative compositions to a location on the patient's tooth, or a dental prosthesis, filling material, or oilier dental work located within a patient's mouth, that has been abraded using the one or more abrasion devices during a dental renewal procedure, wherein the kit container only includes components suitable for use in performing Class I and/or non-invasive dental renewal procedures.

2. The kit as recited in claim 1, wherein the one or more abrasion devices comprise at least one low-speed dental but having a shaft that is designed so as to only mate with the receiving portion of a low-speed dental hand piece but not with the receiving portion of a high-speed dental hand piece, thus preventing use of the at least one low-speed dental bur in a high-speed hand piece.

3. The kit as recited in claim 1, wherein the one or more abrasion devices comprise:

at least one high-speed dental bur having a shaft that is designed to only mate with the receiving portion of a high-speed dental hand piece but not the receiving portion of a low-speed dental hand piece; and an adaptor, removably attached to the shaft of the at least one high-speed dental bur, that modifies the size of the shaft of the high-speed dental bur so as to allow the high-speed dental bur to mate with the receiving portion of a low-speed dental hand piece but not the receiving portion of a high-speed dental hand piece while the adaptor remains attached to the high-speed dental bur.

4. The kit as recited in claim 1, wherein the one or more abrasion devices comprise at least one of a prophylaxis cup or a prophylaxis brush.

5. The kit as recited in claim 4, the kit further comprising at least one prophylaxis composition containing an abrasive material.

6. The kit as recited in claim 1, wherein the kit further comprises at least one of a prophylaxis jet or a device suitable for microabrasia.

7. The kit as recited in claim 1, wherein the one or more dental restorative compositions comprise at least one of a dental cleaning agent, a dental acid etch, a dental primer, a dental bonding agent, or a dental drying agent.

8. The kit as recited in claim 1, wherein the one or more dental restorative compositions comprise at least one of a composite dental resin or a dental sealant.

9. The kit as recited in claim 1, wherein the kit comprises at least one delivery tip having a cannula in a range of 28–32 gauge.

10. The kit as recited in claim 1, wherein the kit comprises at least one delivery tip having a cannula in a range 30–31 gauge.

11. The kit as recited in claim 1, further comprising one or more syringe delivery devices adapted to be selectively couplable with at least one of the delivery tips.

12. The kit as recited in claim 11, each syringe delivery device being preloaded with one of the dental restorative compositions.

13. The kit as recited in claim 1, further comprising one or more syringe delivery devices, wherein at least one syringe delivery device is integrally connected to at least one delivery tip.

14. A kit comprising a pre-packaged set of components specially selected and adapted for use by a dental hygienist or dental technician in safely and effectively performing a noninvasive dental renewal procedure, but not highly invasive dental procedures, the pre-packaged set of components being initially disposed within a kit container prior to use, the components within the kit container comprising:

means for noninvasively abrading a patient's tooth, or a dental prosthesis, filling material, or other dental work located within a patient's mouth, during a non-invasive dental renewal procedure, said means not noninvasively abrading a patient's tooth being unsuitable for highly invasive dental absent modification;

one or more dental restorative compositions suitable for application to a tooth in a Class I an/or non-invasive dental renewal procedure; and one or more delivery tips adapted for delivery of the one or more restorative compositions to a location on the patient's tooth, or dental prosthesis, filling material, or other dental work located within a patient's mouth, that has been abraded using the means for noninvasively abrading a patient's tooth, or a dental prosthesis, filling material, or other dental work located within a patient's mouth, during a dental renewal procedure, wherein the kit container only includes components suitable for use in performing Class I and/or non-invasive dental renewal procedures.

15. The kit as recited in claim 14, wherein the means for noninvasively abrading a patient's tooth, or a dental prosthesis, filling material, or other dental work located within a patient's mouth, comprises a low-speed dental bur configured to only mate with the receiving portion of a low-speed dental hand piece that operates at a speed in a range of 0–50,000 RPM but not with the receiving portion of a high speed dental hand piece that operates at a speed in a range 300,000–500,000 RPM.

16. The kit as recited in claim 15, further comprising a low-speed dental hand piece that operates at a speed in a range of 0–50,000 RPM.

17. The kit as recited in claim 14, wherein the means for noninvasively abrading a patient's tooth, or a dental prosthesis, filling material, or other dental work located within a patient's mouth, comprises a prophylaxis jet high-speed.

18. The kit as recited in claim 14, wherein the means for noninvasively abrading a patient's tooth, or a dental prosthesis, filling material, or other dental work located within a patient's mouth, comprises at least one of a prophylaxis cup or prophylaxis brush having a shaft that is designed to mate with the receiving portion of a low-speed dental hand piece that operates at a speed in a range 0–50,000 RPM.

19. The kit as recited in claim 14, wherein the means for noninvasively abrading a patient's tooth, or a dental prosthesis, filling material, or other dental work located within a patient's mouth, comprises a prophylaxis paste.

20. The kit as recited in claim 14, wherein the one or more dental restorative compositions comprise at least one of a dental cleaning agent, a dental acid etch, a dental primer, a dental bonding agent, a dental drying agent, a dental composite resin, or dental sealant.

21. The kit as recited in claim 14, further comprising a syringe delivery device configured to engage the one or more delivery tips.

22. The kit as recited in claim 14, wherein the kit comprises at least one delivery tip having a cannula in a range of 28–32 gauge.

23. The kit as recited in claim 14, wherein the kit comprises at least one delivery tip having a cannula in a range of 30–31 gauge.

24. A kit conspiring a pre-packaged set of components specially selected and adapted for use by a dental hygienist or dental technician in safely and effectively performing a non-invasive dental renewal procedure, the pre-packaged set of components being initially disposed within a kit container prior to use, the components within the kit container comprising:

one or more low speed dental burs suitable for use in performing at least a portion of a Class I restoration, the one or more low speed dental burs having a shaft that is sized and configured to only mate with the receiving portion of a low-speed dental hand piece that operates at a speed in a range of 0–50,000 but not with the receiving portion of a high-speed dental hand piece that operates at a speed in a range of 300,000–500,000, thus preventing use of the one or more low-speed dental burs in a high-speed hand piece;

one or more dental restorative compositions suitable for application to a tooth in a Class I and/or non-invasive dental renewal procedure; and one or more delivery tips having a cannula in a range of 28–32 gauge for delivery of the one or more restorative compositions to a location on a patient's tooth, or dental prosthesis, filling material, or other dental work located within a patient's mouth, that has been abraded using the one or more low speed dental burs during a Class I restoration;

wherein the kit container only includes components suitable for use in performing Class I and/or non-invasive dental renewal procedures.

25. The kit as recited in claim 24, further comprising a low-speed dental hand piece that operates at a speed in a range of 0–50,000.

26. The kit as recited in claim 24, further comprising one or more syringe delivery devices configured to store and deliver the one or more dental restorative compositions to the location on the patient's tooth, or a dental prosthesis, filling material, or other dental work located within a patient's mouth, during a Class I restoration, the one or more syringe delivery devices being configured to engage the one or more delivery tips.

27. The kit as recited in claim 24, wherein the one or more restorative compositions comprise at least one of a dental cleaning agent, a dental acid etch, a dental primer, a dental bonding agent, a dental drying agent, a dental composite resin, or a dental sealant.

28. A kit comprising a pre-packaged set or components specially selected and adapted for use by a dental hygienist or dental technician in safely and effectively performing tooth prophylaxis in a dental renewal procedure, the pre-package set or components being initially disposed within a kit container prior in use, the components within the kit container comprising:

at least one prophylaxis device suitable for tooth prophylaxis;

one or more dental restorative compositions suitable for application to a tooth subjected to tooth prophylaxis; and one or more delivery tips having a cannula in a range of 28–32 gauge for delivery of the one or more restorative compositions to a location on a patient's tooth, or a dental prosthesis, filling material, or other dental work located within a patient'mouth, that has been abraded using the at least one prophylaxis device during a Class I restoration, wherein the kit container only includes components suitable for use in performing Class I and/or non-invasive dental renewal procedures.

29. The kit as recited in claim 28, wherein the prophylaxis device comprises at least one of a prophylaxis cup or prophylaxis brush having a shaft designed to mate with the receiving portion of a low-speed dental hand piece that operates at a speed in a range of 0–50,000.

30. The kit as recited in claim 28, further comprising a prophylaxis paste.

31. The kit as recited in claim 28, further comprising one or more syringe delivery devices configured to store and deliver the one or more dental restorative compositions to the location on a patient's tooth, or a dental prosthesis, filling material, or other dental work located within a patient's mouth during a Class I restoration, the one or more syringe delivery devices being configured to engage the one or more delivery tips.

32. The kit as recited in claim 28, wherein the one or more dental restorative compositions comprises at least one of a dental cleaning agent, a dental acid etch, a dental primer, a dental bonding agent, a dental drying agent, a dental composite resin, or a dental sealant.

33. A kit comprising a pre-packaged set of components specially selected and adapted for use by a dental hygienist or dental technician in safely and effectively performing a non-invasive dental renewal procedure, the pre-packaged set of components being initially disposed within a kit container prior to use, the components within the kit container comprising:

one or more abrasion devices adapted to mate with a low-speed dental hand piece that operates at a speed in a range 0–50,000 RPM and configured so as to noninvasively abrade at least one of a patient's tooth, or a dental prosthesis, filling material, or other dental work located within a person's mouth, during a Class I dental restoration and/or non-invasive dental renewal procedure;

one or more dental restorative compositions suitable for application to a tooth in a Class I and/or non-invasive dental renewal procedure; and one or more delivery tips having a cannula in a range of 30–31 gauge, the one or more delivery tips adapted for delivery of the one or more restorative compositions to a location on the patient's tooth, or a dental prosthesis, filling material, or other dental work located within a patient's mouth, that has been abraded using the one or more abrasion devices during a Class I restoration and/or non-invasive dental renewal procedure, wherein the kit container only includes components suitable for use in performing Class I and/or non-invasive dental renewal procedures.

34. The kit as recited in claim 33, wherein the one or more abrasion devices comprise at least one of a dental bur, a prophylaxis cup, or a prophylaxis brush.

35. The kit as recited in claim 33, wherein the one or more dental restorative compositions comprise at least one of a dental cleaning agent, a dental acid etch, a dental primer, a dental bonding agent, a dental drying agent, a dental composite resin, or a dental sealant.

36. A method for enabling a dental hygienist or dental technician to safely and effectively perform a non-invasive dental renewal procedure, the method comprising:

providing to a dental hygienist or dental technician a dental renewal kit comprising a kit container within which are initially pre-packaged (a) at least one abrasion device suitable for use in performing at least a portion of a Class I and/or non-invasive dental renewal procedure (b) at least one dental restorative composition suitable for Class I and/or non-invasive dental renewal procedures, and (c) at least one delivery tip;

removing one or more abrasion devices from the kit container;

the dental hygienist or dental technician non-invasively abrading a dental site using the one or more abrasion devices and a low-speed dental hand piece operating at a speed in a range of 0–50,000 the dental site comprising at least one of a patient's tooth, or a dental prosthesis, filling material, or other dental work located within the patient's mouth;

removing one or more dental restorative composition and one or more delivery tips from the kit container; and the dental hygienist or dental technician applying the one or more dental restorative compositions to the dental site using the one or more delivery tips.

37. The method as recited in claim 36, wherein abrading at least one of a patient's tooth, or a dental prosthesis, filling material, or other dental work located within the patient's mouth, comprises using a low-speed dental bur designed to only mate with the low-speed dental hand piece and not with a high-speed dental hand piece that operates at a speed in a range of 300,000–500,000.

38. The method as recited in claim 36, wherein abrading at least one of a patient's tooth, a dental prosthesis, filling material, or other dental work located within the patient's mouth comprises applying a mildly abrasive prophylaxis paste with one of a prophylaxis cup or a prophylaxis brush to the patient's tooth, dental prosthesis, filling material, or other dental work located within the patient's mouth.

* * * * *

UNITED STATES PATENT AND TRADEMARK OFFICE
CERTIFICATE OF CORRECTION

PATENT NO.      : 6,905,335 B2
DATED           : June 14, 2005
INVENTOR(S)     : Melba Bumgarner It is certified that error appears in the above-identified patent and that said Letters Patent is hereby corrected as shown below:

Column 1,
Line 36, change "procedures" to -- procedure --.

Column 4,
Line 28, change "deliver" to -- delivery --.

Column 5,
Line 60, change "3–3D" to -- 3A–3D --.

Column 6,
Line 22, change "kits" to -- kit --.

Column 8,
Line 2, before "inserted" insert -- to be --.
Line 9, before "provided" change "is" to -- all --.

Column 10,
Line 4, after "portion" change "at" to -- of --.
Line 22, change "oilier" to -- other --.
Line 29, after "dental" change "but" to -- bur --.

Column 11,
Line 24, after "said means" change "not" to -- for --.
Line 26, before "absent modification;" insert -- procedures --.
Lines 56 and 57, change "jet high-speed." to -- jet. --.

UNITED STATES PATENT AND TRADEMARK OFFICE
CERTIFICATE OF CORRECTION

PATENT NO. : 6,905,335 B2
DATED : June 14, 2005
INVENTOR(S) : Melba Bumgarner

It is certified that error appears in the above-identified patent and that said Letters Patent is hereby corrected as shown below:

Column 12,
Line 17, change "conspiring" to -- comprising --.
Line 43, change "restoration;" to -- restoration, --.

Signed and Sealed this

Twenty-eighth Day of February, 2006

JON W. DUDAS
*Director of the United States Patent and Trademark Office*